US008189192B2

(12) United States Patent
Huening et al.

(10) Patent No.: US 8,189,192 B2
(45) Date of Patent: May 29, 2012

(54) VOLUME PHASE GRATING SPECTROMETERS AND RELATED METHODS AND SYSTEMS

(75) Inventors: Pete Huening, Clayton, NC (US); Robert H. Hart, Cary, NC (US); Eric L. Buckland, Hickory, NC (US)

(73) Assignee: Bioptigen, Inc., Durham, NC (US)

( * ) Notice: Subject to any disclaimer, the term of this patent is extended or adjusted under 35 U.S.C. 154(b) by 460 days.

(21) Appl. No.: 12/491,546

(22) Filed: Jun. 25, 2009

(65) Prior Publication Data

US 2010/0014081 A1   Jan. 21, 2010

Related U.S. Application Data

(60) Provisional application No. 61/075,402, filed on Jun. 25, 2008.

(51) Int. Cl.
*G01J 3/28* (2006.01)
(52) U.S. Cl. ....................................................... 356/328
(58) Field of Classification Search .................. 396/329; 248/187.1; 356/328
See application file for complete search history.

(56) References Cited

U.S. PATENT DOCUMENTS

| 3,869,212 | A | * | 3/1975 | Burcher et al. ................ 356/328 |
| 4,611,888 | A | * | 9/1986 | Prenovitz et al. .............. 600/112 |
| 6,281,506 | B1 | * | 8/2001 | Fujita et al. ............. 250/370.09 |
| 7,480,058 | B2 | | 1/2009 | Zhao et al. |
| 2005/0094147 | A1 | * | 5/2005 | Yaroslavsky et al. ......... 356/417 |
| 2008/0030728 | A1 | | 2/2008 | Nguyen |

FOREIGN PATENT DOCUMENTS
EP    0 541 449 A2   11/1992

OTHER PUBLICATIONS

Notification of Transmittal of the International Search Report and the Written Opinion of the International Searching Authority, or the Declaration, PCT/US2009/003776, Dec. 30, 2009.
Hyvarinen et al., "Direct sight imaging spectrograph: a unique add-on component brings spectral imaging to industrial applications," Proceedings of the SPIE, SPIE, Bellingham, VA, US, vol. 3302, Jan. 28, 1998, pp. 165-175.
Invitation to Pay Additional Fees and, Where Applicable, Protest Fee, International Application No. PCT/US2009/003776, Nov. 3, 2009, 8 pages.
Traub, W.A., "Constant-dispersion grism spectrometer for channeled spectra," J. Opt. Soc. A vol. 7 No. 9, 1990, pp. 1779-1791.
Notification Concerning Transmittal of International Preliminary Report on Patentability; International Preliminary Report on Patentability; Written Opinion of the International Searching Authority corresponding to International Application No. PCT/US2009/003776; Date of mailing: Jan. 13, 2011; 12 pages.

* cited by examiner

*Primary Examiner* — Kara E Geisel
(74) *Attorney, Agent, or Firm* — Myers Bigel Sibley & Sajovec (57) ABSTRACT

A Spectrometer is provided including a camera and an axial symmetric camera mount configured to receive the camera and to rotate. The spectrometer furthers include an input for providing optical radiation to a spectrometer system; a diffraction grating for dispersing the optical radiation along a prescribed plane; at least one lens for focusing wavelength-dispersed light onto at least one array of a detector of optical radiation, wherein the camera has at least one linear array of elements for detecting optical radiation; a mechanical housing, wherein the axial symmetric camera mount is configured to couple the camera to the mechanical housing; and a means for rotating the camera coupled to the mechanical housing about an axis. Related systems and methods are also provided.

17 Claims, 12 Drawing Sheets

VOLUME PHASE GRATING SPECTROMETERS AND RELATED METHODS AND SYSTEMS

CLAIM OF PRIORITY

The present application claims priority from U.S. Provisional Application No. 61/075,402, filed Jun. 25, 2008, the disclosure of which is hereby incorporated herein by reference as if set forth in its entirety.

STATEMENT OF GOVERNMENT SUPPORT

This invention was made with government support under grant number 2R44EY015585 awarded by National Institutes of Health, National Eye Institute. The United States Government has certain rights in this invention.

FIELD

The present invention relates to imaging and, more particularly, to optical coherence tomography (OCT) and related methods, systems and computer program products.

BACKGROUND

Optical coherence tomography (OCT) is a noninvasive imaging technique that provides microscopic tomographic sectioning of biological samples. By measuring singly backscattered light as a function of depth, OCT fills a valuable niche in imaging of tissue ultrastructure, providing subsurface imaging with high spatial resolution (~2.0-10.0 µm) in three dimensions and high sensitivity (>110 dB) in vivo with no contact needed between the probe and the tissue.

In biological and biomedical imaging applications, OCT allows for micrometer-scale imaging non invasively in transparent, translucent, and/or highly-scattering biological tissues. The longitudinal ranging capability of OCT is generally based on low-coherence interferometry, in which light from a broadband source is split between illuminating the sample of interest and a reference path. The interference pattern of light reflected or backscattered from the sample and light from the reference delay contains information about the location and scattering amplitude of the scatterers in the sample. In time-domain OCT (TDOCT), this information is typically extracted by scanning the reference path delay and detecting the resulting interferogram pattern as a function of that delay. The envelope of the interferogram pattern thus detected represents a map of the reflectivity of the sample versus depth, generally called an A-scan, with depth resolution given by the coherence length of the source. In OCT systems, multiple A-scans are typically acquired while the sample beam is scanned laterally across the tissue surface, building up a two-dimensional map of reflectivity versus depth and lateral extent typically called a B-scan. The lateral resolution of the B-scan is approximated by the confocal resolving power of the sample arm optical system, which is usually given by the size of the focused optical spot in the tissue.

The time-domain approach used in conventional OCT, including commercial instruments, such as Carl Zeiss Meditec's StratusOCT® and Visante® products, has been successful in supporting biological and medical applications, and numerous in vivo human clinical trials of OCT reported to date have utilized this approach.

An alternate approach to data collection in OCT has been shown to have significant advantages both in reduced system complexity and in increased signal-to-noise ratio (SNR). This approach involves acquiring the interferometric signal generated by mixing sample light with reference light at a fixed group delay as a function of optical wavenumber. Two distinct methods have been developed which use this Fourier domain OCT (FDOCT) approach. The first, generally termed Spectral-domain or spectrometer-based OCT (SDOCT), uses a broadband light source and achieves spectral discrimination with a dispersive spectrometer in the detector arm. The second, generally termed swept-source OCT (SSOCT) or optical frequency-domain imaging (OFDI), time-encodes wavenumber by rapidly tuning a narrowband source through a broad optical bandwidth. Both of these techniques may allow for a dramatic improvement in SNR of up to 15.0-20.0 dB over time-domain OCT, because they typically capture the A-scan data in parallel. This is in contrast to previous-generation time-domain OCT, where destructive interference is typically used to isolate the interferometric signal from only one depth at a time as the reference delay is scanned.

Spectrometer-based implementations of FDOCT have the potential of advantaged phase stability, as the source and detection modules are passive. However, in practice spectrometer based designs for high resolution imaging have been shown to have some shortcomings. High resolution spectrometers rely on a highly dispersive element with optics that provide approximately constant magnification imaging across a broad focal plane. Optical designs using transmission volume phase holograms or reflective Eschelle gratings for achieving desired results are well known and applied in many laboratory set-ups.

A difficulty arises in developing a spectrometer that is readily manufacturable and passively stable in the face of environmental perturbation. One solution to environmental stability has been proposed by Wei et. al. utilizing an actively controlled fold mirror as discussed in U.S. Pat. No. 7,480,058. This system has the capability to continually adjust alignment to optimize attributes of the spectrograph.

SUMMARY

Some embodiments of the present invention provide a spectrometer including a camera and an axial symmetric camera mount configured to receive the camera and to rotate.

In further embodiments of the present invention, the spectrometer may further include an input for providing optical radiation to a spectrometer system; a diffraction grating for dispersing the optical radiation along a prescribed plane; at least one lens for focusing wavelength-dispersed light onto at least one array of a detector of optical radiation, wherein the camera has at least one linear array of elements for detecting optical radiation; a mechanical housing, wherein the axial symmetric camera mount is configured to couple the camera to the mechanical housing; and a means for rotating the camera coupled to the mechanical housing about an axis.

In still further embodiments of the present invention, the camera may be mounted to the mechanical housing via the camera mount such that a plane defined by a central axis of the at least one detector array and a normal to the at least one detector array is co-planar with a plane defined by the grating-dispersed optical radiation; the normal to the at least one detector array is at a prescribed angle with respect to a central optical axis of the mechanical housing; and the angle is such that the dispersed wavelength components are in substantially equivalent focus along the at least one detector array.

In some embodiments of the present invention, the camera mount may include a housing-side bore and a camera-side bore. The mechanical housing may be coupled to the housing-side of the camera mount and the axis of the housing-side bore is substantially parallel to a central optical axis of the housing. The camera may be coupled to the camera-side of the camera mount and the axis of the camera-side bore is substantially parallel to the normal of the at least one detector array. The housing-side bore may intersect the camera side bore at the prescribed angle with respect to the camera-side bore.

In further embodiments of the present invention, the camera mount may include a bore and at least one wedge, the mechanical housing may be coupled to the camera mount, the camera may be coupled to the camera mount, and a normal to the at least one wedge may be at the prescribed angle with respect to a central optical axis of the housing.

In still further embodiments of the present invention, the mechanical housing may include a grating and a grating mount. The grating may be pre-aligned in the grating mount before assembly into the mechanical housing. In certain embodiments, the grating may be a grating-prism (grism) pair.

In some embodiments of the present invention, the prescribed angle between a central optical axis of the housing and a normal to the at least one detector array may be substantially zero degrees.

In further embodiments of the present invention, the spectrometer may be a constant-dispersion spectrometer.

In still further embodiments of the present invention, the grating may be a transmission grating.

In some embodiments of the present invention, the mechanical housing may include an adjustable port to accept an optical fiber; the adjustable port may include adjustment to control the direction of output of light from the optical fiber in one or more lateral directions; and the adjustable port may include adjustment to control the direction of output of light from the optical fiber in one or more rotational directions.

In further embodiments of the present invention, the adjustable port may be a means for adjusting the axial position of the input fiber In still further embodiments of the present invention, the mechanical housing may be a unibody housing. The unibody housing may include an irregular internal surface for suppression of stray light.

In some embodiments of the present invention, the spectrometer may be used in a spectral domain optical coherence tomography (SDOCT) system.

Further embodiments of the present invention provide a method for aligning a spectrometer for optimum focus, the spectrometer including a camera and an associated camera mount, the method including rotating the camera 90 degrees about the camera mount; shining a light source in a range of the spectrometer; and adjusting a focus of the spectrometer until a least number of pixels is illuminated by the narrowband light source.

Still further embodiments of the present invention provide a method for aligning a spectrometer, the spectrometer including a camera with at least one linear array of elements of detecting optical radiation, the method comprising rotating the camera with at least one linear array of detection elements substantially 90 degrees with respect to a dispersive plane of the spectrometer; directing optical radiation through the spectrometer onto the at least one linear array of detection elements; measuring an illumination of a subset of elements on the at least one linear array; adjusting a focal position of optical radiation; rotating the camera with at least one linear array of detection elements such that the camera is substantially parallel to the dispersive plane of the spectrometer; directing the optical radiation through the spectrometer onto the at least one linear array of detection elements; measuring an illumination of a subset of elements on the at least one linear array; and adjusting a rotational position of the camera.

DETAILED DESCRIPTION

The present invention will be described more fully hereinafter with reference to the accompanying figures, in which embodiments of the invention are shown. This invention may, however, be embodied in many alternate forms and should not be construed as limited to the embodiments set forth herein.

Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention as defined by the claims. Like numbers refer to like elements throughout the description of the figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this invention belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

A high performance spectrometer for optical coherence tomography should be mechanically and thermally stable during shipping, storage and in service. An active feedback system or a system that requires frequent adjustments in the field has significant disadvantages. Accordingly, some embodiments of the present invention provide an appropriately designed passive system that improves ease of initial alignment, as the degrees of freedom associated with an active system are removed. The costs of manufacturing and assembling the dynamic system are eliminated, as is the need for software overhead to manage a feedback loop. Furthermore, robust passive systems in accordance with some embodiments of the present invention may increase the portability of the imaging system, opening the door to broader applications requiring frequent transport and movement of the system as will be discussed herein with respect to FIGS. 1 through 16 of the present application.

In conventional systems, optical components are mounted to a heavy optical plate. This gives rise to complex expansion modes and uneven stress distributions. Because the centerlines of the deformations occur at a distance from the optical axis, amplification results. This can be further amplified by the optics.

In some embodiments of the present invention, the optics are housed inside a block with a consistent cross sectional area to the extent possible. This symmetry was carried through the rest of the parts making up the spectrometer. The centerline of the housing is coaxial with the optical axis. This constrains the thermal expansion to the least sensitive direction, reduces or possibly eliminates amplification, and, because the moment of inertia is increased, the optical assembly is much more rigid.

Some embodiments of the present invention provide high performance spectrometers with improved mechanical and thermal properties, and methods for simplified alignment of the same. The specific embodiments discussed herein utilize a transmission Volume Phase Hologram architecture, but the concepts are as readily applied to other dispersive architectures, including Eschelle grating spectrographs without departing from the scope of the present invention.

Volume Phase Grating Spectrometers (VPGS) according some embodiments of the present invention include an optical system that images a broad spectrum from an input port to a spectrally dispersed line image at a focal plane; a fiber input port that includes mechanics for aligning the fiber along up to five axes; a collimator; a machined block (unibody) that houses gratings, lenses and possibly mirrors in proximity; and a line array detector mount. The line array detector mount may include one or more of axial focal adjustment; angular focal adjustment; rotation for alignment of the dispersed spectrum focal plane to the detector array. In some embodiments of the present invention, the VPGS may further include an assembly and alignment process that separates focus optimization from alignment optimization for ease of assembly.

In some embodiments of the present invention the line array detector may include one or more parallel arrays of detector elements, and the detector arrays may be individually addressable, or may be addressed in combination through a process of binning.

Figure 1:
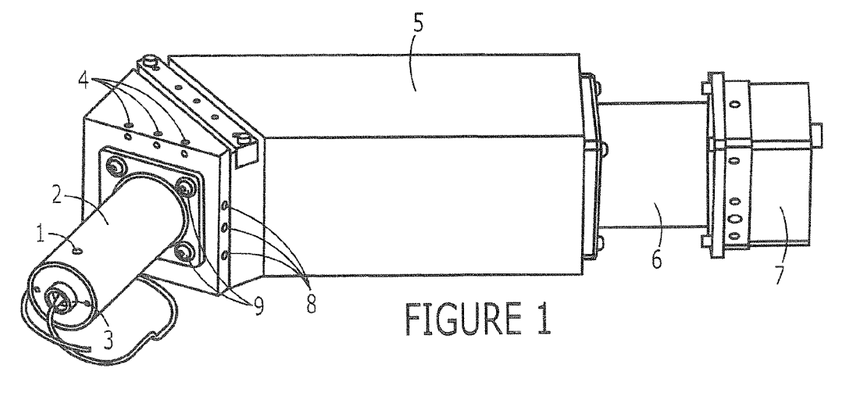
FIG. 1 is a diagram illustrating an isometric view of Volume Phase Grating Spectrometers in accordance with some embodiments of the present invention.

Referring first to FIG. 1, a diagram illustrating an isometric view of the VPGS in accordance with some embodiments of the present invention will be discussed. As illustrated in FIG. 1, the VPGS includes a Fiber alignment fine adjustment 1, a fiber alignment mount 2, an input fiber focus mount 3, an input fiber coarse vertical adjustment 4, a spectrometer unibody 5, an array detector mount 6, an array detector 7, an input fiber course horizontal adjustment 8 and an input fiber course adjustment locks 9.

Figure 2:
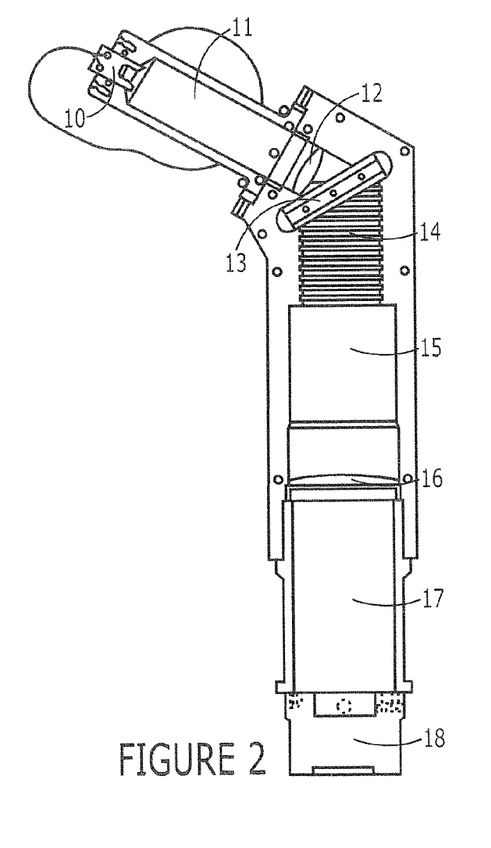
FIG. 2 is a diagram illustrating a cut away view of Volume Phase Grating Spectrometers in accordance with some embodiments of the present invention.

Referring now to FIG. 2, a diagram illustrating a cut away view of the VPGS Spectrometer according to some embodiments of the present invention will be discussed. As illustrated in FIG. 2, the VPGS further includes an input fiber focus mount 10, a fiber alignment mount 11, a fiber collimator lens 12, a grating assembly 13, a stray light suppression surface 14, a spectrometer unibody 15, an array detector mount 17 and array detector 18.

In some embodiments of the present invention, the VPGS uses a transmission Volume Phase Hologram. The optical quality of the Volume Phase Hologram Spectrometer (RVPHS) according to some embodiments of the present invention is based upon the combination of a volume phase holographic diffraction grating illustrated in FIG. 2 (element 13), with a long focal length imaging system illustrated in FIG. 2 (element 16), which may result in improved image quality at the optical focal plane which impinges on the array detector as shown in FIG. 1 (element 7) and FIG. 2 (element 18). Volume phase holographic transmission gratings are known for their high efficiency, low polarization dependence, and low stray light characteristics. In addition to the optical quality of the grating, the long focal length imaging system may result in a unity magnification imaging system with very low spherical and chromatic aberrations and long depth of focus. Specific optical designs are known in the art. However, alignment tends to be very difficult, and the imaging system requires a high degree of mechanical and thermal stability.

In some embodiments of the present invention, the diffractive element may include a grating-prism pair (grism). The grism may in some embodiments of the present invention be designed to create an un-deviated dispersive axis, for example to simplify machining of the unibody housing. Alternatively, the grism may be designed to create a constant-dispersion spectrometer to nominally linearize the spectrometer in wavenumber as discussed in *Constant-dispersion grism spectrometer for channeled spectra* by W. A. Traub (J. Opt. Soc. A Vol 7 No. 9, 1990, 1779-1791).

Thus, according to some embodiments of the present invention, a unibody type construction is used in which all optical components comprising the imaging system illustrated in FIG. 2 (elements 12, 13, and 17) of the spectrometer are mounted within a single optical block as illustrated in FIG. 1 (element 5) and again in FIG. 2 (element 15). In some embodiments, the spectrometer interior construction includes stray light reducing surfaces to suppress the fundamental diffraction order of the volume phase grating as shown in FIG. 2 (element 14). The array detector mount illustrated in FIG. 1 (element 6) and FIG. 2 (element 17) is rotationally symmetric allowing the detector to be rotated about 90 degrees to act as a line width detector to aid in the focus of the spectrometer optics. The array detector mount 17 also provides improved thermal isolation of the array detector as illustrated in FIG. 1 (element 7) and again in FIG. 2 (element 18) due to the isolation of the array detector mount from adjacent support structures allowing for adequate air flow around the array detector. The coupling of the array detector mount to the spectrometer unibody further confines any thermal expansion to the direction of the optical axis of the imaging system resulting in focus deviations which typically have a negligible effect on system performance due to the long depth of focus characteristic of the imaging system design.

The VPGS according to some embodiments of the present invention may also include a four axis input fiber mount as illustrated in FIG. 1 (element 2) and FIG. 2 (element 11) to provide stable optical and mechanical performance along with ease of manufacture. The four axis mount consists of coarse adjustment screws for vertical alignment as illustrated in FIG. 1 (element 4) and coarse adjustment screws for horizontal alignment as illustrated in FIG. 1 (element 8) along with elevation angle control via the fine adjustment screws as illustrated in FIG. 1 (element 1). The fourth axis control is focus adjustment along the optical axis via the input fiber focus mount as illustrated in FIG. 1 (element 3) and FIG. 2 (element 10). It will be understood that the VPGSs provided in FIGS. 1 and 2 of the present application are provided for examplary purposes only and, therefore, embodiments of the present invention are not limited to this configuration. For example, a fifth axis control for azimuth can be added without departing from the scope of the present invention. However, the fifth axis control may not generally be necessary, as lateral misalignment may lead to a shift in spectral centration that can be managed during a separate calibration process.

Figure 8:
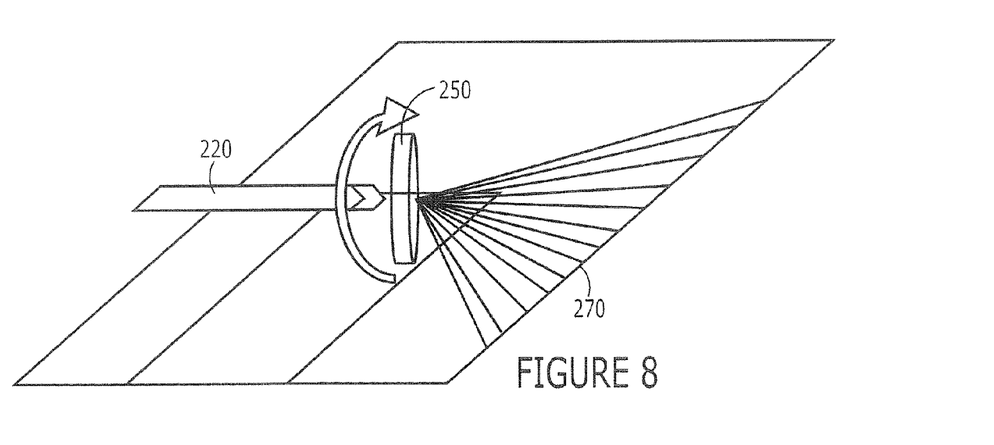
FIG. 8 is a diagram illustrating a plane of spectral dispersion through a transmission Volume Phase Grating according to some embodiments of the present invention
Figure 9:
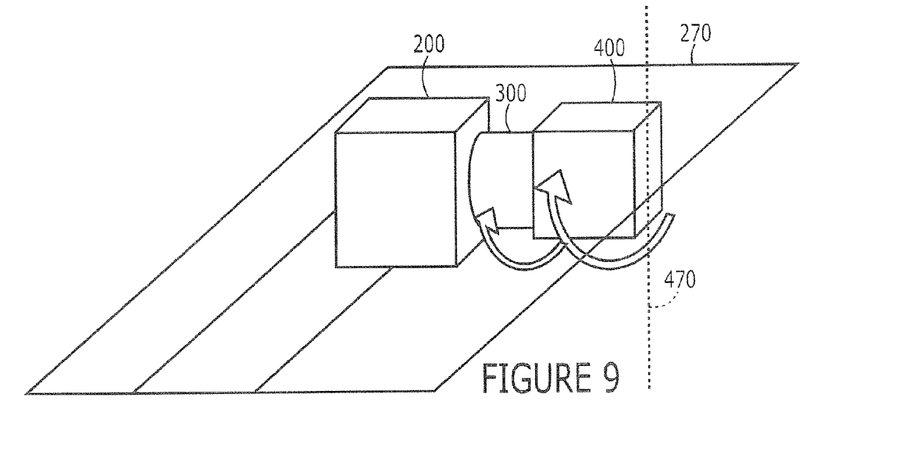
FIG. 9 is a block diagram illustrating the rotation of the detector array to an orthogonal orientation with respect to the dispersive plane to facilitate focus according to some embodiments of the present invention
Figure 10:
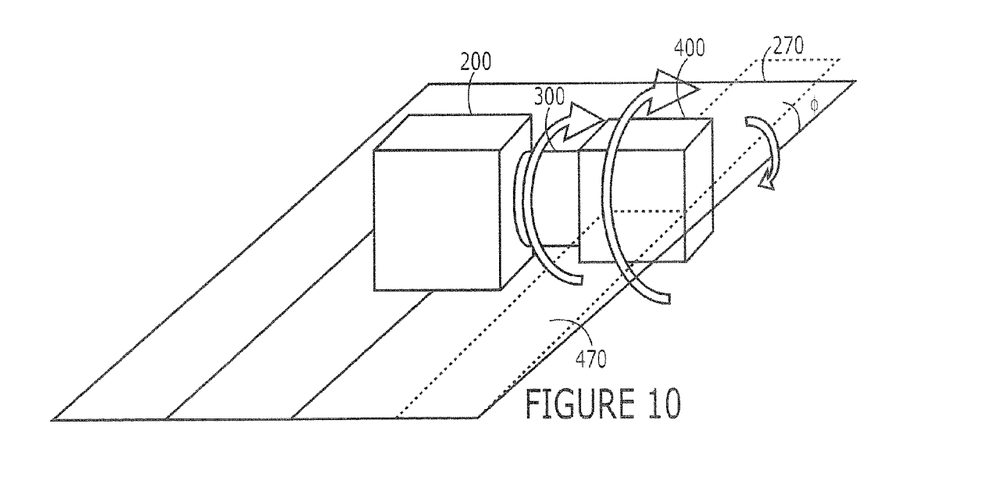
FIG. 10 is a block diagram illustrating the rotation of the detector array to a parallel orientation with respect to the dispersive plane to facilitate fine alignment according to some embodiments of the present invention

The alignment for a system in accordance with some embodiments of the present invention will now be discussed. The grating is pre-oriented in the grating assembly and installed into the unibody. The lenses are installed into the machined positions in the unibody. The line scan camera is affixed the camera mount, and the mount is inserted, but not locked into the unibody. The input fiber is affixed to a puck that is inserted into the fiber alignment mount. As illustrated in FIG. 8, the output spectrum from the fiber 220 is dispersed by the grating 250 to form a dispersive plane 270. As further illustrated in FIG. 9, the camera body 400 is rotated using the detector mount 300 about 90 degrees with respect to the unibody housing 200 so that the dispersed spectrum is nominally orthogonal to, and centered on the axis of the line scan array 470. The axial position of the fiber puck and/or the axial position of the camera body are adjusted to optimize the central focus of the spectrum with respect to the line scan array. Focus is monitored by minimizing the spread of power on pixels of the line scan camera in the 90 degree configuration. In some embodiments, only one pixel is illuminated, but the degree of illumination of neighboring pixels is typically never a delta function, owing to diffraction and aberrations. Once focus is optimized, axial positions of the input fiber and/or camera mount are locked into place, and the camera is rotated to the nominal 0 degree position. Final fine alignment is mediated through lateral and elevation adjustment of the fiber alignment mount (x,y, theta), rotation of the camera mount to maximize the overlap of the dispersed spectrum with the line scan array of the camera as illustrated in FIG. 10. Post-alignment the entire fiber alignment mount and camera mount are locked securely in place via the locking screws illustrated in FIG. 1 (element 9).

Figure 3:
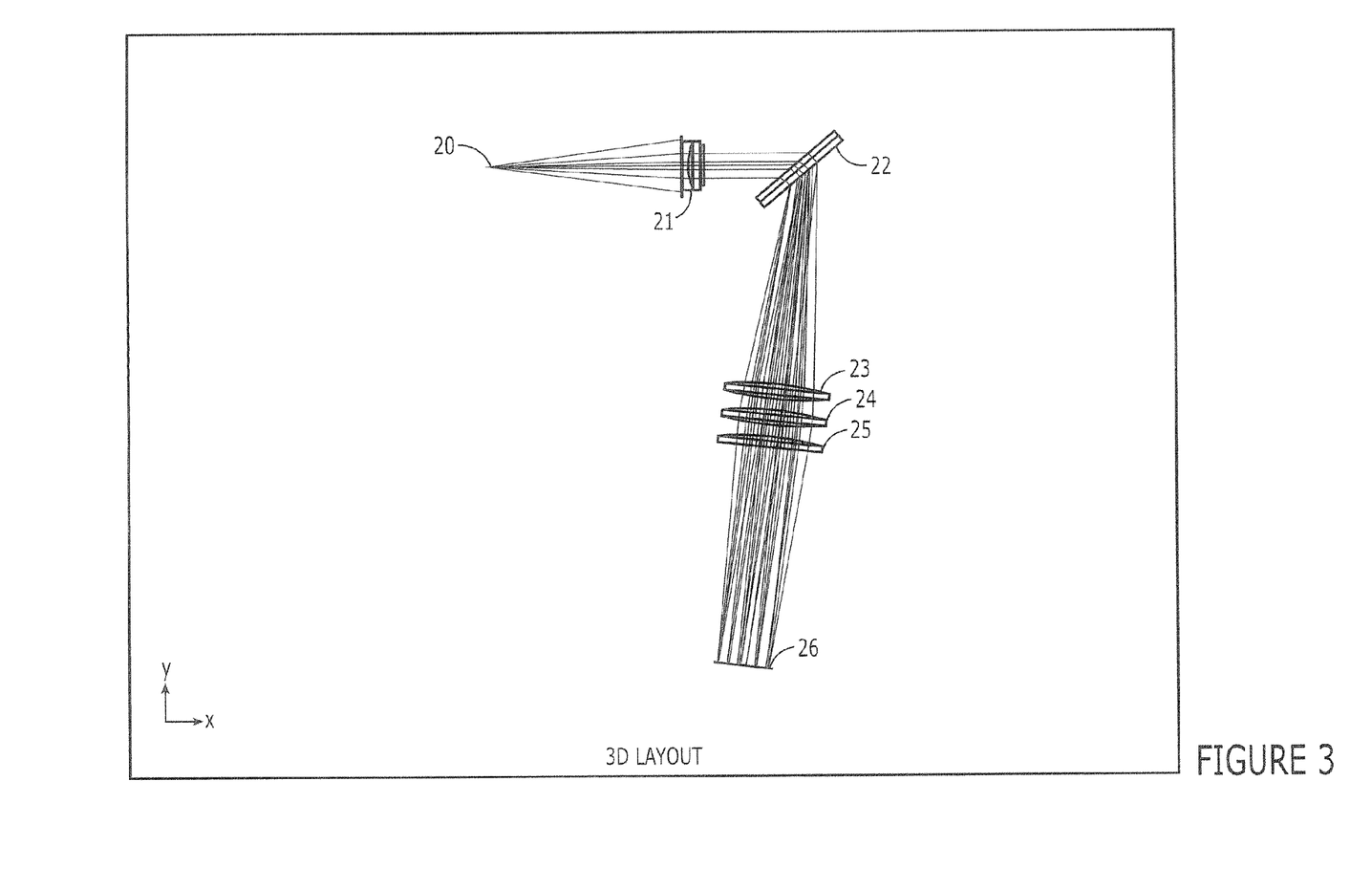
FIG. 3 is a diagram illustrating an optical layout for 1310 nm Spectrometer, 100 nm Bandwidth according to some embodiments of the present invention.
Figure 4:
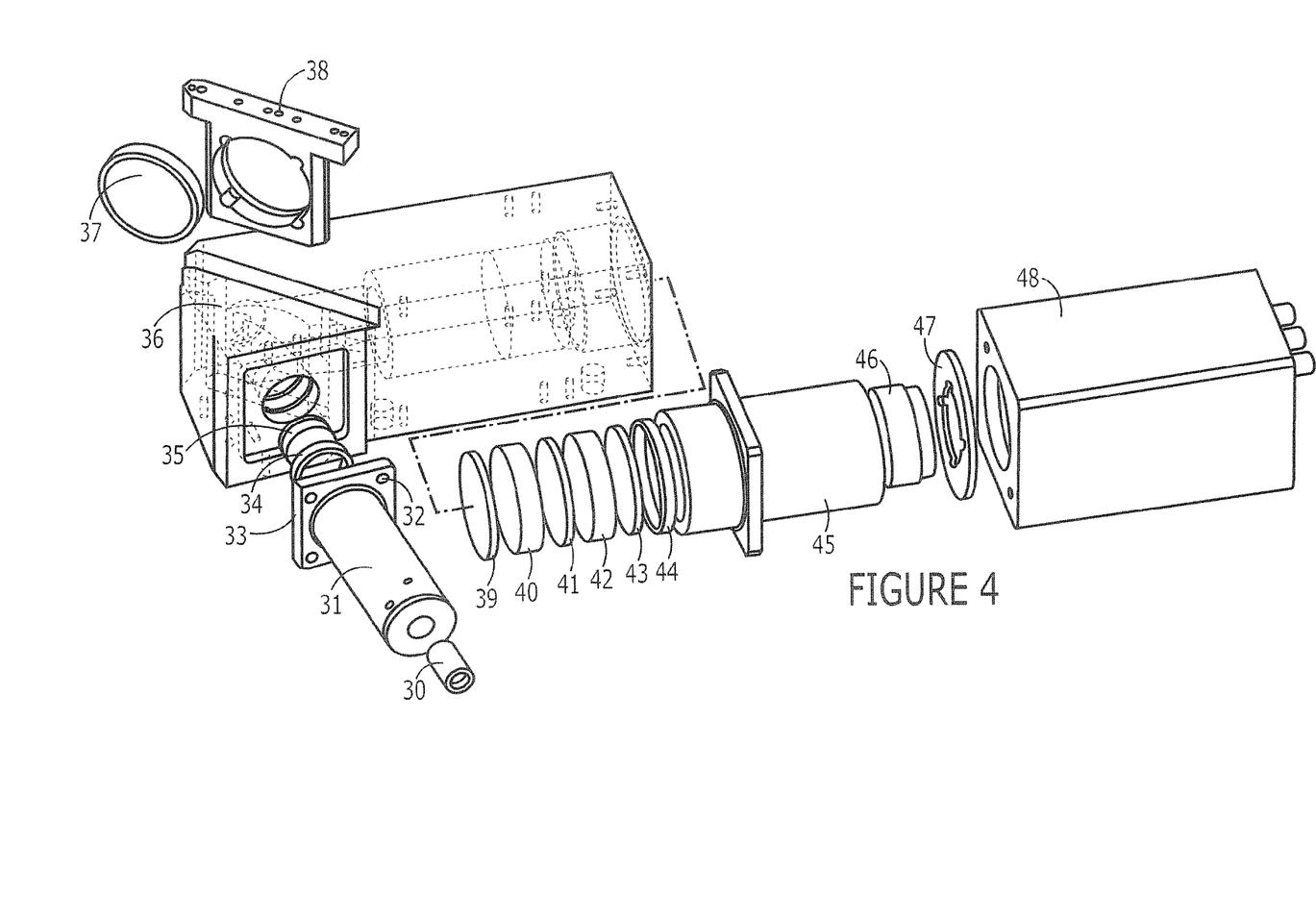
FIG. 4 is a diagram illustrating an opto-mechanical Design for 1310 nm, 100 nm Bandwidth Spectrometer in accordance with some embodiments of the present invention.
Figure 7:
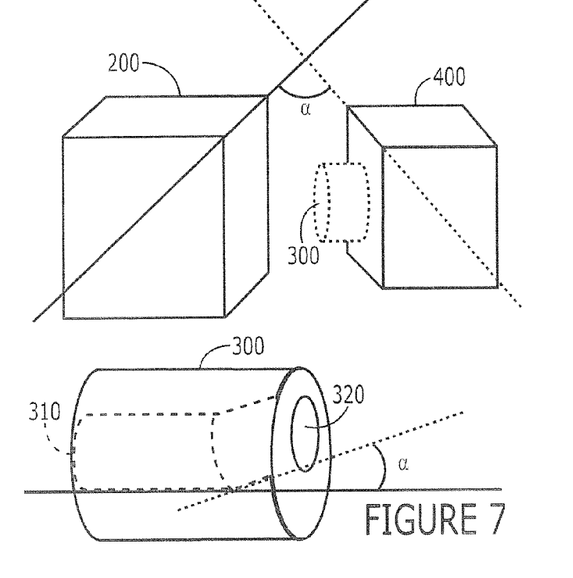
FIG. 7 is a block diagram illustrating the angular relationship between the central optical axis of the dispersive system and the orientation of the detector array according to some embodiments of the present invention

Referring now to FIGS. 3 and 4, diagrams illustrating an optical layout and mechanical design, respectively, of a 1310 nm Spectrometer in accordance with some embodiments of the present invention will be discussed. FIG. 3 is a ray trace of the 1310 nm Spectrometer optical design in accordance with some embodiments of the present invention. Shown is the input fiber represented as the origin of the light rays 20, the 100 millimeter focal length near infrared optimized achromatic collimating lens 21, the 1145 line pair per millimeter Volume Phase Holographic grating 22, the first element of the objective lens 23 which is a 300 millimeter focal length bi-convex singlet lens, the second element of the objective lens 24 which is a 400 millimeter focal length plano-convex singlet lens, the third element of the objective lens 25 which is also a 400 millimeter focal length plano-convex singlet lens, and the detector array 26 which is a 1024 element Indium Gallium Arsenide linear photo detector array. The normal to the detector array is set at an angle alpha with respect to the optical axis of the dispersive imaging system to compensate for focus as a function of wavelength as shown in FIG. 7. In some embodiments the angle alpha equals about 1.5 degrees. In some embodiments of the present invention, the angle is set by milling an angular offset bore 320 within the detector mount 300, such that a normally opposed cylindrical mounting plate 450 on the detector 400 attaches snugly to the mount 300 at an angle theta with respect to the central optical axis. The central optical axis is defined by the input bore 310 on the unibody 200 side of the detector mount.

Referring now to FIG. 4, an exploded view of the opto-mechanical Design for 1310 nm, 100 nm Bandwidth Spectrometer illustrating internal components thereof according to some embodiments of the present invention will be discussed. The optical train starts with the input fiber focus mount 30, which fits into the fiber alignment mount 31 which mounts to the spectrometer unibody 36 via shoulder screws 32 and locking screws 33. The 100 millimeter focal length near infrared optimized achromatic collimating lens 34 also fit directly into the spectrometer unibody 36 and is retained in place by the threaded retainer ring 35. The 1145 line pair per millimeter Volume Phase Holographic grating 37 is aligned and bonded into the grating mount 38 thus making the grating mount assembly which is inserted into the spectrometer unibody 36 and fastened in place with machine screws. The diffracted light from the grating is then focused via the three element objective lens. The first element of the objective lens is the 300 millimeter focal length bi-convex singlet lens 39 which is inserted into the spectrometer unibody 36 followed by a lens spacer 40 followed by the second element of the objective lens which is a 400 millimeter focal length plano-convex singlet lens 41 followed by a second lens spacer 42 and the third element of the objective lens 43 which is also a 400 millimeter focal length plano-convex singlet lens. In some embodiments, all the lens elements are fixed in place by the lens retaining ring 44. The 1024 element Indium Gallium Arsenide linear photo detector array 48 is mounted to the camera adapter plate 47 which accepts a threaded camera mount 46 which in turn slides into the camera mounting tube 45 allowing the camera to rotate during the alignment phase. The camera mounting tube 45 is bolted to the spectrometer unibody 36 using machine screws. The inter-sleeving sections of the camera mount 46, the camera mounting tube 45 and the spectrometer unibody produced a very mechanically robust interface with a high degree of concentricity for accurate alignment. The camera mounting tube 45 also has an angle offset machined in which constrains the camera to the proper angle relative to the optical axis improving the image quality by compensating for at 1.5 degree tilt in the image plane relative to the 1024 element Indium Gallium Arsenide linear photo detector array 48.

Figure 5:
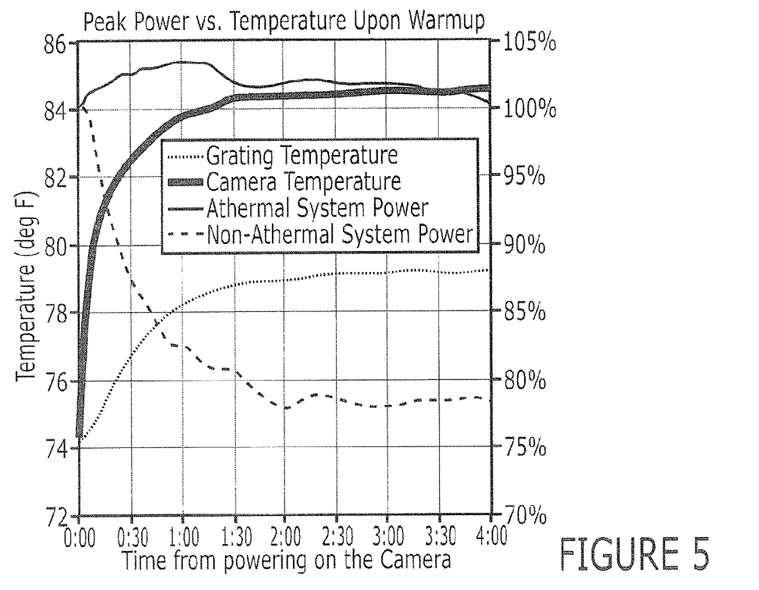
FIG. 5 is a graph illustrating optical throughput comparison of athermal designs during warm up testing according to some embodiments of the present invention inventive versus a non-athermal design.
Figure 6:
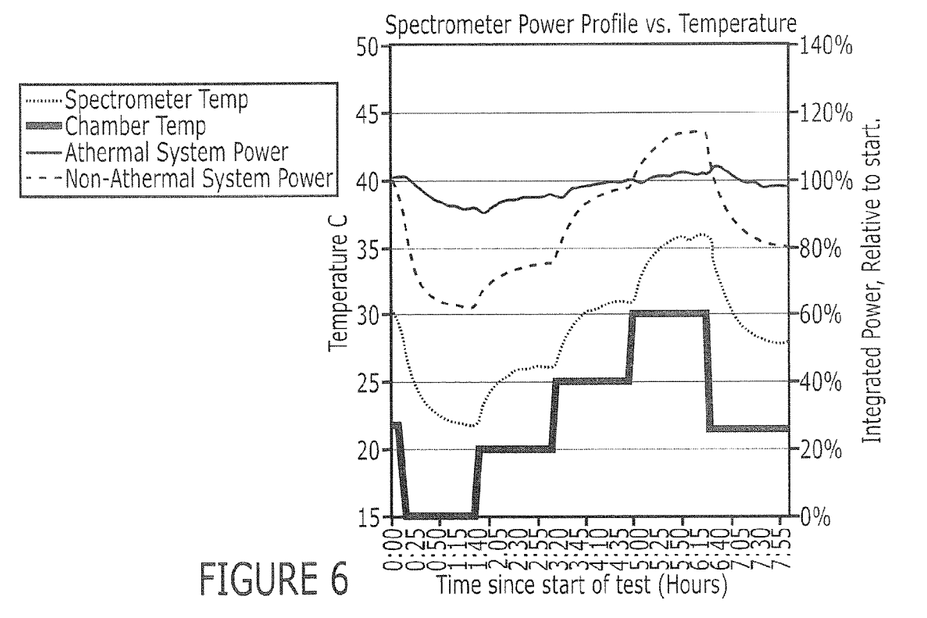
FIG. 6 is a graph illustrating optical throughput comparison of an athermal design during thermal cycling (15° C. to 30° C.) according to some embodiments of the present invention versus a non-athermal design according to some embodiments of the present invention.

Thermal performance of VPGSs in accordance with some embodiments of the present invention will now be discussed with respect to FIGS. 5 and 6. FIGS. 5 and 6 illustrate results of thermal performance of the VPGSs in accordance with some embodiments of the present invention. FIGS. 5 and 6 are graphs illustrating performance of a system according to some embodiments of the present invention during warm-up and a thermal cycle, respectively. With respect to FIG. 5, system temperatures were recorded at the camera, and at the grating assembly. With respect to FIG. 6, system temperatures were recorded in the thermal chamber and on the spectrometer body.

FIG. 5 illustrates performance during warm up, where the camera heats 10° F. from room temperature (74° F.) to 84° F., as seen by the double solid line in the figure. The warm up is due to the camera, while the grating, reflected in the dotted line, warms up to 79° F. over the same four hour period due to thermal transfer characteristics. A poorly athermalized spectrograph design (dashed line) shows a power drift (decrease) of over 20%. The spectrograph of the design according to some embodiments of the present invention (solid line) is stable during warm up to better than 5%.

Similarly, FIG. 6 illustrates that during thermal cycling the spectrograph of the design according to some embodiments of the present invention (solid line) is stable during thermal variations observed in use, from 15° C. to 30° C. (double solid line), which throughput varies less than 5%, where the non-athermalized design (dashed line) fluctuates over an excursions of +20% to −40% in throughput. Note that the poorly athermalized spectrograph power (dashed line) is highly correlated to the temperature variation of the spectrograph body (dotted line) during the test, whereas the athermalized spectrograph optical performance (solid line) is substantially independent of the body temperature.

Figure 11:
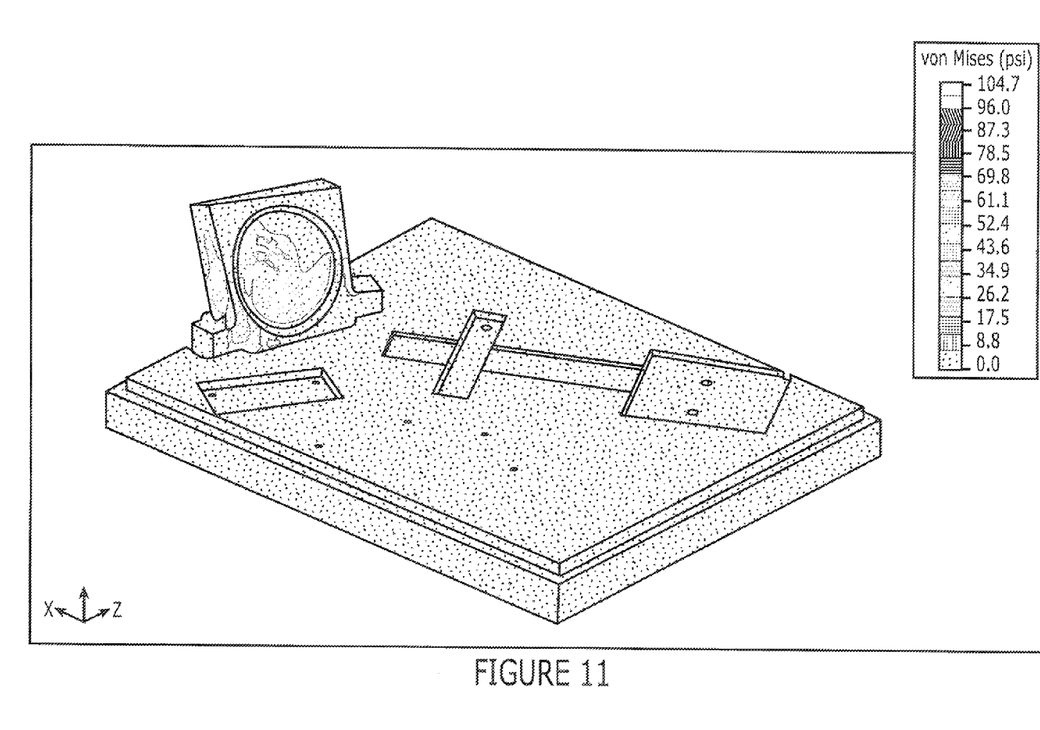
FIG. 11 is a stress diagram showing the stress that yields a 50% power reduction on an exemplary plate spectrometer according to some embodiments of the present invention
Figure 12:
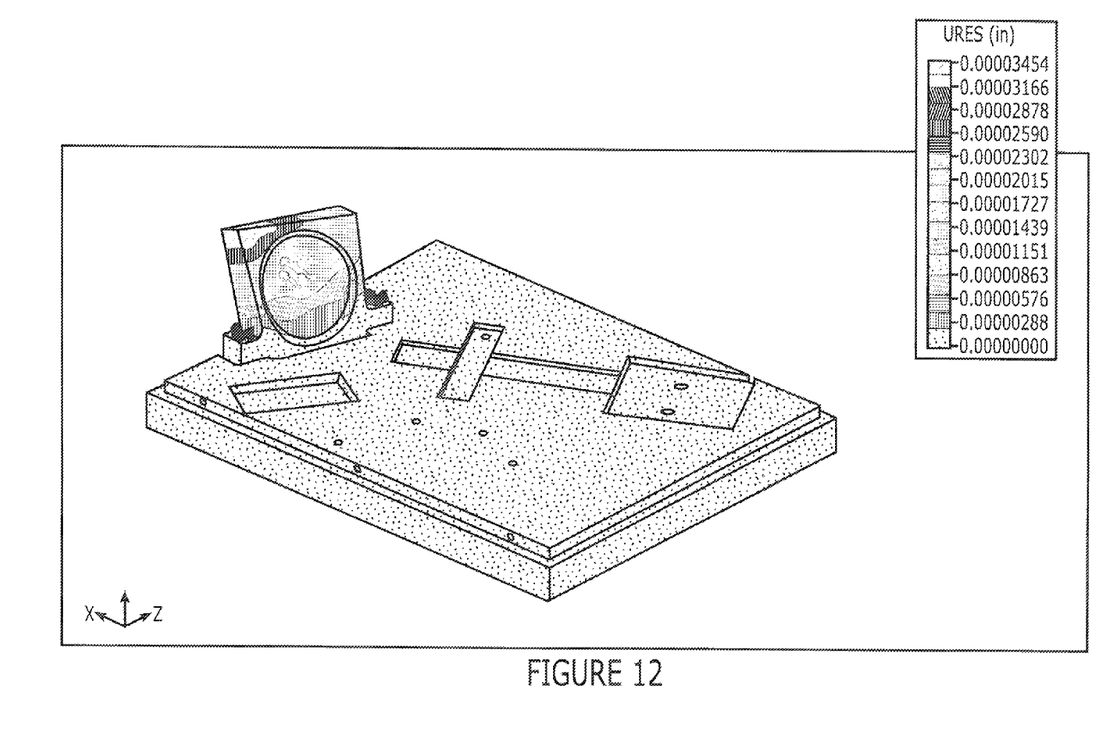
FIG. 12 is a diagram showing the strain that yields a 50% power reduction on an exemplary plate spectrometer according to some embodiments of the present invention

The mechanical advantage has been modeled comparing a plate assembly and the unibody construction according to some embodiments of the present invention. The plate design as shown in FIG. 11 was used to analyze spectrometer sensitivity. A force was applied as shown to a ½ inch thick mirror mount which had a ½ inch thick mirror bonded around its circumference. The force was increased until the output signal was reduced by 50% and found to be only 2 pounds. From an FEA analysis, the highest stresses developed were less than can be expected from bolting two surfaces together that are not absolutely flat or from moving the assembly from one place to another. Even more surprising were the unobservable but optically critical small displacements involved (see FIG. 12).

Figure 13:
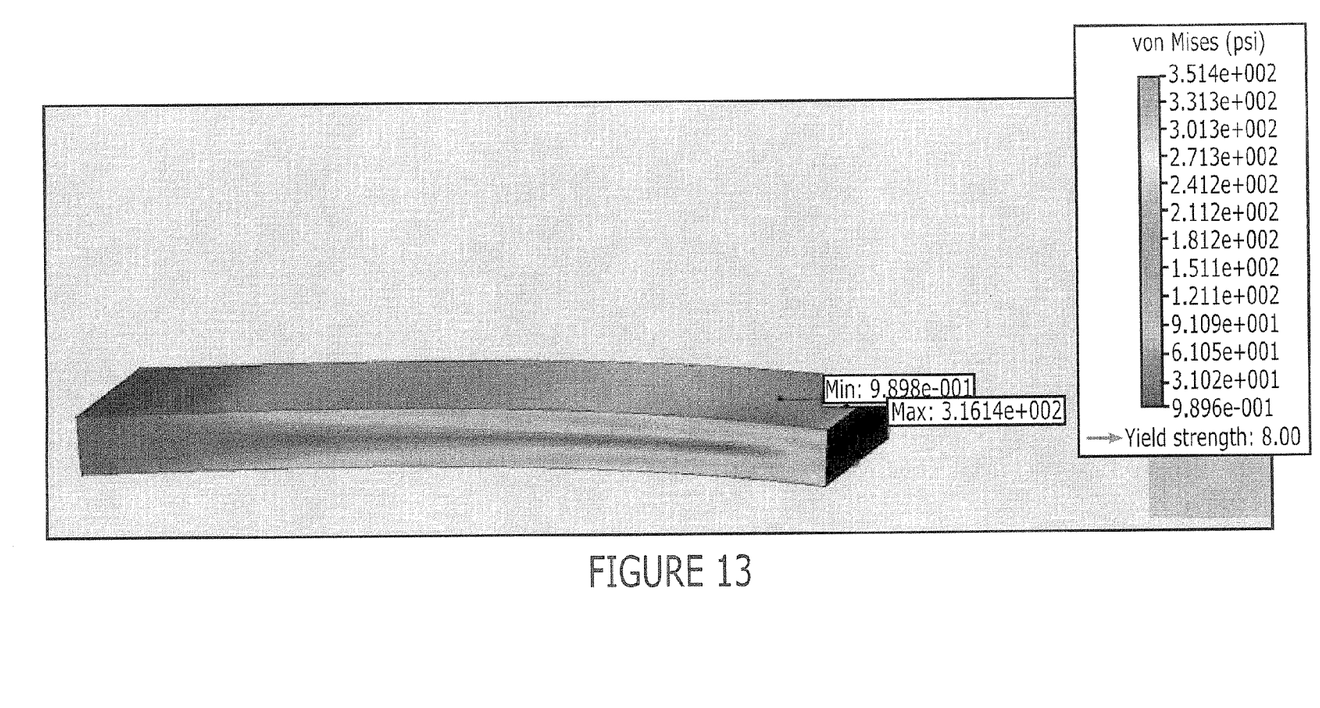
FIG. 13 is a stress diagram showing the stress due to a 10 lb load on one end of an exemplary plate spectrometer according to some embodiments of the present invention
Figure 14:
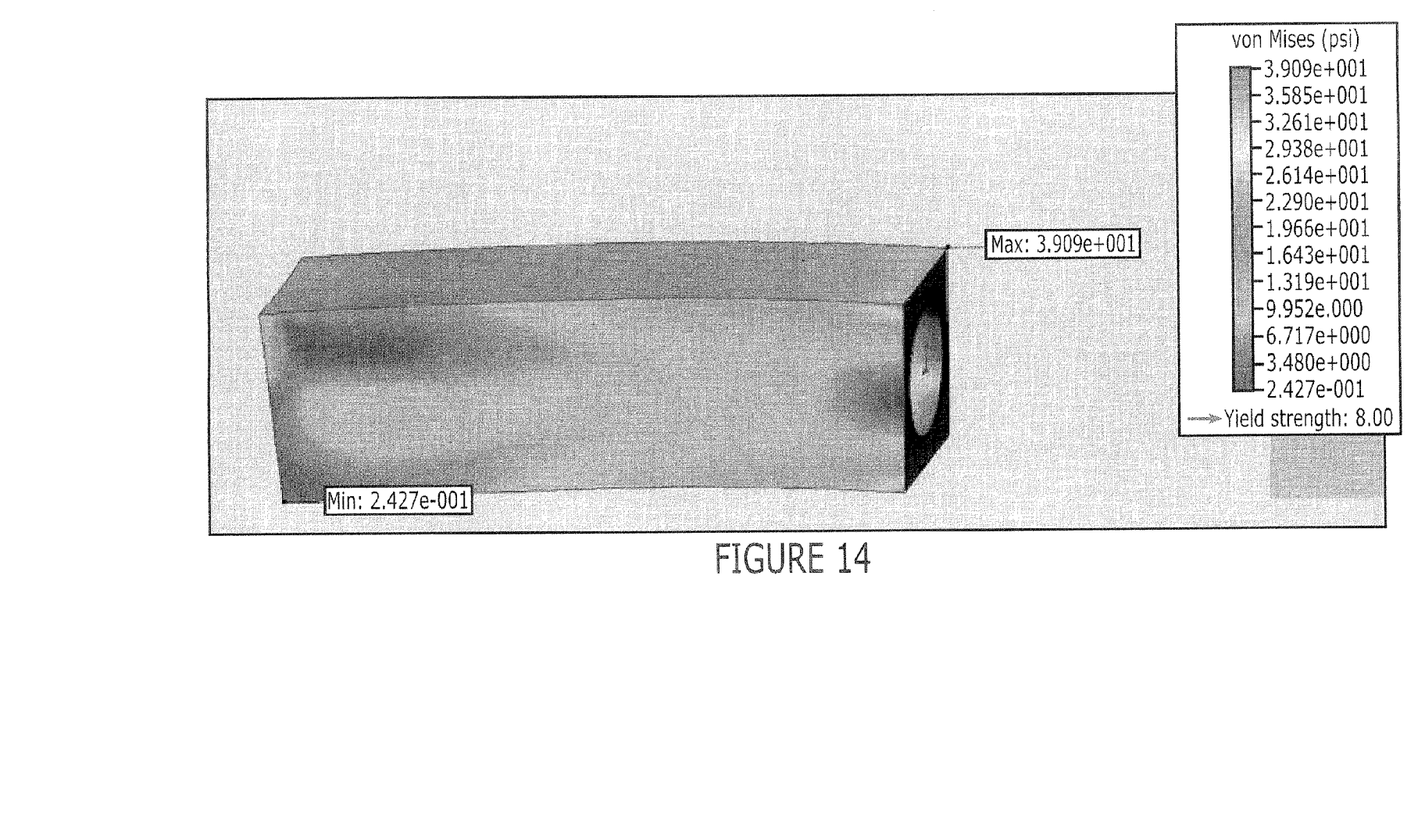
FIG. 14 is a stress diagram showing the stress due to a 10 lb load on one end of an exemplary unibody spectrometer according to some embodiments of the present invention
Figure 15:
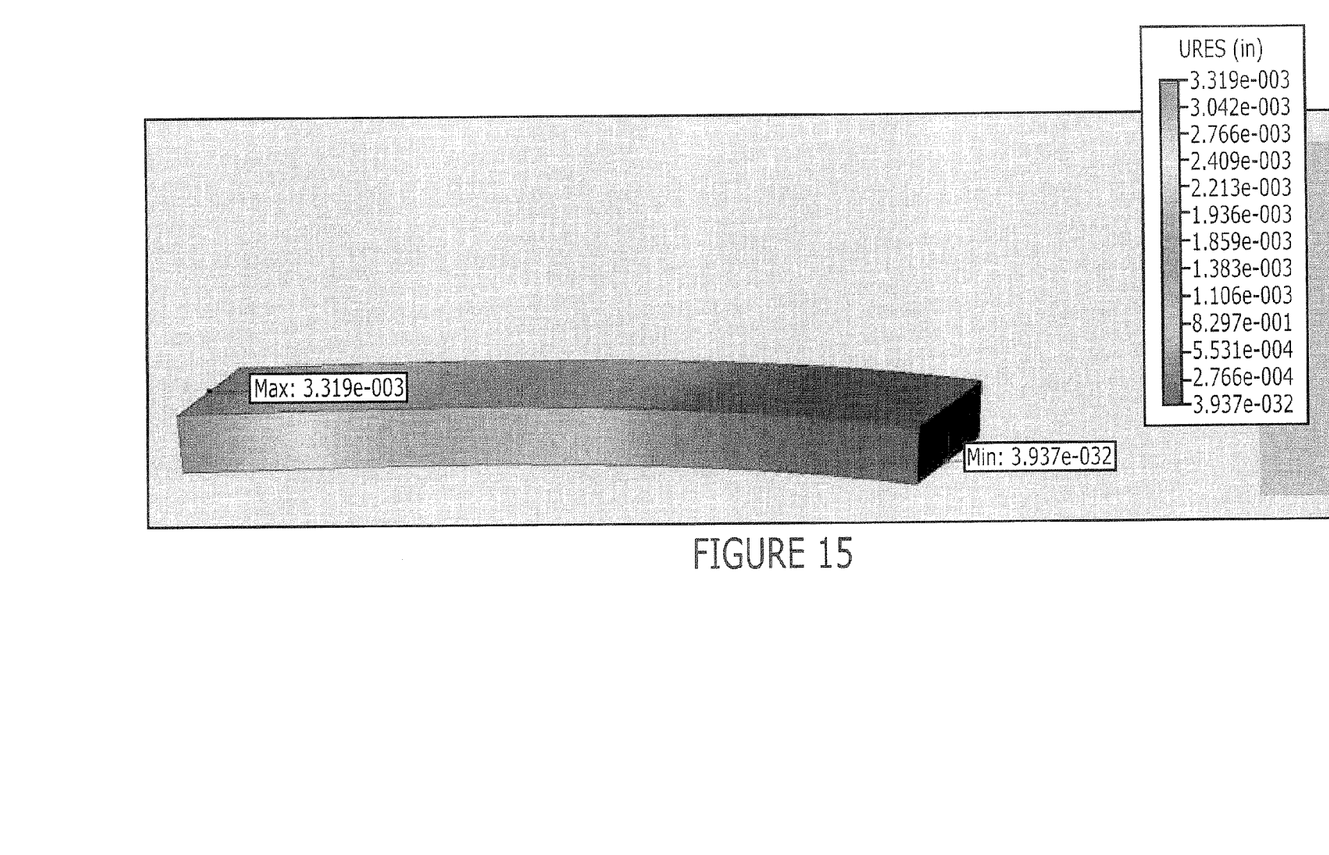
FIG. 15 is a corresponding diagram showing the strain due to a 10 lb load on one end of an exemplary plate spectrometer according to some embodiments of the present invention
Figure 16:
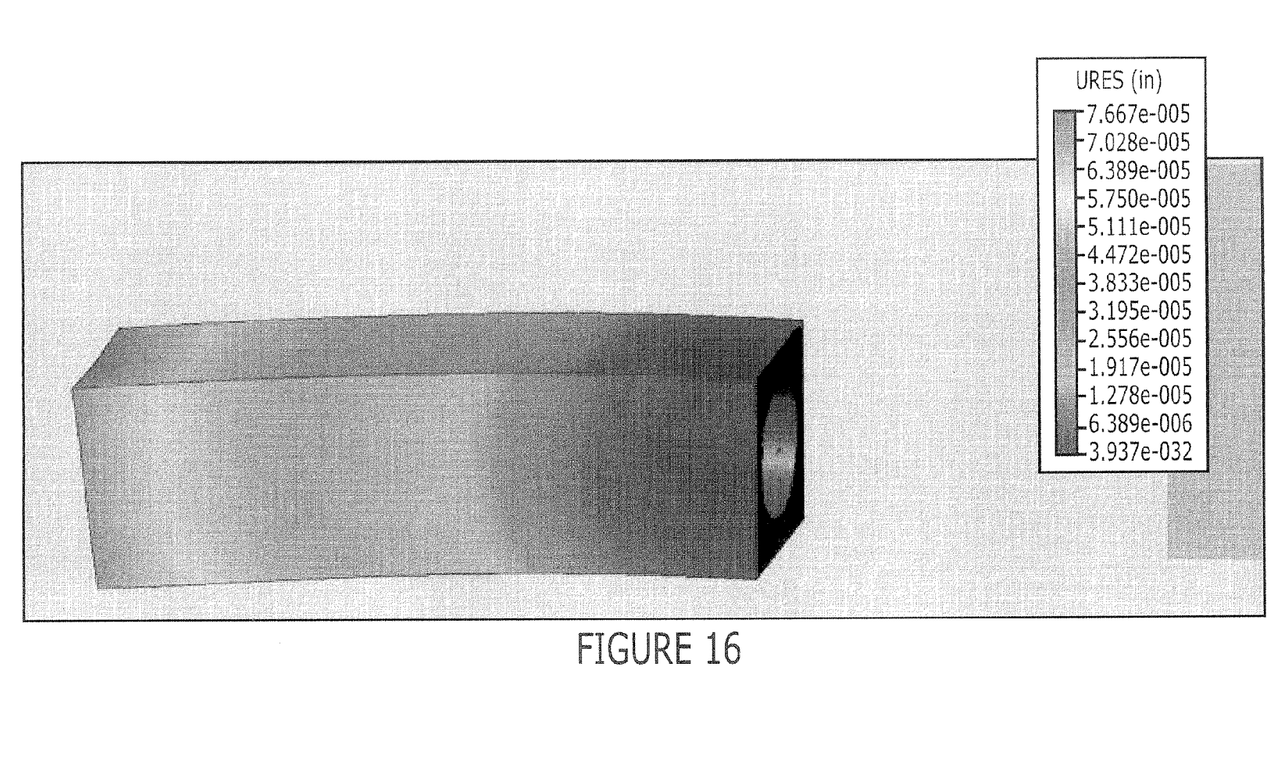
FIG. 16 is a diagram showing the strain due to a 10 lb load on one end of an exemplary unibody spectrometer according to some embodiments of the present invention.

Using FEA, geometries representing a plate design of the size considered for plate and for unibody designs were compared for relative stiffness. In both cases, one end of the model was restrained and a 10 pound load was applied at the opposite end to simulate expected loads. FIGS. 13 and 14 show the stresses developed. From FIGS. 15 and 16, it can be seen that the unibody approach reduces the displacements by more than an order of magnitude. The plate had to be increased to 2.75 (75.6 cu in of Al as modeled) inches thick before the deflections were reduced to the level of the unibody. The optical components see an amplified motion due to their moment arm with respect to the plate. In comparison the total unibody diameter, including all optical elements is only 3 (51 cu in of Al as modeled) inches tall, and there is no differential moment arm for the optics. The unibody construction has better mechanical stiffness, a higher moment of inertia for the optics, and weighs 33% less than a comparably stiff plate solution.

As discussed briefly above, performance of the Volume Phase Grating Spectrometer unibody construction coupled with the thermally stable array detector mount in conjunction with the long focal length imaging system and the four axis adjustable fiber alignment mount in accordance with some embodiments of the present invention may create a superior performing spectrometer system, which is both thermally and mechanically stable, relatively easy to align and therefore relatively easy to manufacture in volume.

Accordingly, some embodiments of the present invention provide a high performance spectrometer design that provides high optical resolution with ease of alignment, low stray light along with excellent thermal and mechanical stability.

In the drawings and specification, there have been disclosed exemplary embodiments of the invention. However, many variations and modifications can be made to these embodiments without substantially departing from the principles of the present invention. Accordingly, although specific terms are used, they are used in a generic and descriptive sense only and not for purposes of limitation, the scope of the invention being defined by the following claims.

That which is claimed is:
1. A spectrometer comprising:
a camera;
an axial symmetric camera mount configured to receive the camera and to rotate;
an input for providing optical radiation to a spectrometer system;
a diffraction grating for dispersing the optical radiation along a prescribed plane;
at least one lens for focusing wavelength-dispersed light onto at least one array of a detector of optical radiation, wherein the camera has at least one linear array of elements for detecting optical radiation;
a mechanical housing, wherein the axial symmetric camera mount is configured to couple the camera to the mechanical housing; and
a means for rotating the camera coupled to the mechanical housing about an axis.

2. The spectrometer of claim 1, wherein the camera is mounted to the mechanical housing via the camera mount such that:
a plane defined by a central axis of the at least one detector array and a normal to the at least one detector array is co-planar with a plane defined by the grating-dispersed optical radiation;
the normal to the at least one detector array is at a prescribed angle with respect to a central optical axis of the mechanical housing; and
the angle is such that the dispersed wavelength components are in substantially equivalent focus along the at least one detector array.

3. The spectrometer of claim 2:
wherein the camera mount comprises a housing-side bore and a camera-side bore;
wherein the mechanical housing is coupled to the housing-side of the camera mount and the axis of the housing-side bore is substantially parallel to a central optical axis of the housing;
wherein the camera is coupled to the camera-side of the camera mount and the axis of the camera-side bore is substantially parallel to the normal of the at least one detector array; and
wherein the housing-side bore intersects the camera side bore at the prescribed angle with respect to the camera-side bore.

4. The spectrometer of claim 2:
wherein the camera mount comprises a bore and at least one wedge;
wherein the mechanical housing is coupled to the camera mount;
wherein the camera is coupled to the camera mount; and
wherein a normal to the at least one wedge is at the prescribed angle with respect to a central optical axis of the housing.

5. The spectrometer of claim 1, wherein the mechanical housing comprises a grating and a grating mount.

6. The spectrometer of claim 5, wherein the grating is pre-aligned in the grating mount before assembly into the mechanical housing.

7. The spectrometer of claim 5, wherein the grating comprises a grism pair.

8. The spectrometer of claim 7, wherein the prescribed angle between a central optical axis of the housing and a normal to the at least one detector array is substantially zero degrees.

9. The spectrometer of claim 7, wherein the spectrometer is a constant-dispersion spectrometer.

10. The spectrometer of claim 5, wherein the grating is a transmission grating.

11. The spectrometer of claim 1:
wherein the mechanical housing comprises an adjustable port to accept an optical fiber;
wherein the adjustable port includes adjustment to control the direction of output of light from the optical fiber in one or more lateral directions; and
wherein the adjustable port includes adjustment to control the direction of output of light from the optical fiber in one or more rotational directions.

12. The spectrometer of claim 11, wherein the adjustable port comprises a means for adjusting the axial position of the input fiber.

13. The spectrometer of claim 1, wherein the mechanical housing comprises a unibody housing.

14. The spectrometer of claim 13, wherein the unibody housing comprises an irregular internal surface for suppression of stray light.

15. The spectrometer of claim 1, wherein the spectrometer system comprises a spectral domain optical coherence tomography (SDOCT) system.

16. A method for aligning a spectrometer for optimum focus, the spectrometer including a camera and an associated camera mount, the method comprising:
rotating the camera 90 degrees about the camera mount;
directing optical radiation in a wavelength range of the spectrometer and rotated camera; and
adjusting a focus of the spectrometer until a least number of pixels is illuminated by a narrowband light source.

17. A method for aligning a spectrometer, the spectrometer including a camera with at least one linear array of elements of detecting optical radiation, the method comprising:
rotating the camera with at least one linear array of detection elements substantially 90 degrees with respect to a dispersive plane of the spectrometer;
directing optical radiation through the spectrometer onto the at least one linear array of detection elements;
measuring an illumination of a subset of elements on the at least one linear array;
adjusting a focal position of optical radiation;
rotating the camera with at least one linear array of detection elements, such that the camera is substantially parallel to the dispersive plane of the spectrometer;
directing the optical radiation through the spectrometer onto the at least one linear array of detection elements;
measuring an illumination of a subset of elements on the at least one linear array; and
adjusting a rotational position of the camera.

* * * * *